US010512955B2

United States Patent
Antonini

(10) Patent No.: US 10,512,955 B2
(45) Date of Patent: Dec. 24, 2019

(54) SYSTEM AND METHOD TO CONTROL A BIOGAS COLLECTION PLANT

(71) Applicant: Antonini Marco Ditta Individuale, Cesena (IT)

(72) Inventor: Marco Antonini, Cesena (IT)

(73) Assignee: ANTONINI MARCO DITTA INDIVIDUALE, Cesena (IT)

( * ) Notice: Subject to any disclaimer, the term of this patent is extended or adjusted under 35 U.S.C. 154(b) by 0 days.

(21) Appl. No.: 15/775,785

(22) PCT Filed: Nov. 14, 2016

(86) PCT No.: PCT/IB2016/056844
§ 371 (c)(1),
(2) Date: May 11, 2018

(87) PCT Pub. No.: WO2017/081671
PCT Pub. Date: May 18, 2017

(65) Prior Publication Data
US 2018/0326464 A1    Nov. 15, 2018

(30) Foreign Application Priority Data

Nov. 13, 2015  (IT) .......................... 102015000072559

(51) Int. Cl.
*B09B 1/00* (2006.01)
*C12M 1/34* (2006.01)
(52) U.S. Cl.
CPC ................ *B09B 1/006* (2013.01); *B09B 1/00* (2013.01); *C12M 41/36* (2013.01); *C12M 41/40* (2013.01); *Y02W 30/35* (2015.05)

(58) Field of Classification Search
CPC .......... B09B 1/006; B09B 1/00; C12M 41/40; C12M 41/36; Y02W 30/35
(Continued)

(56) References Cited

U.S. PATENT DOCUMENTS 4,670,148 A    6/1987  Schneider
8,221,626 B2 *  7/2012  Sassow .................. C12M 21/04
                                                         210/603

(Continued)

FOREIGN PATENT DOCUMENTS

EP           0904857 A1    3/1999
WO    2017/081671 A1    5/2017

*Primary Examiner* — Fred Prince
(74) *Attorney, Agent, or Firm* — Schwabe Williamson & Wyatt, PC

(57) ABSTRACT

System to control a biogas collection plant having a manifold and a plurality of collection units connecting respective capturing wells to the manifold and having respective biogas flow rate regulation valves; the system having a control board with a pressure sensor, a methane sensor, an oxygen sensor, a biogas pressure monitoring network connecting the pressure sensor to the collection units by means of respective control valves, and a chemical biogas monitoring network connecting the methane sensor and the oxygen sensor to the collection units by means of as many control valves; the control board selectively controlling the control valves to measure pressure, methane concentration and oxygen concentration of the biogas in the collection units and controlling the regulation valves as a function of the pressure and methane and oxygen concentration values measured.

18 Claims, 2 Drawing Sheets

(58) Field of Classification Search
USPC .............. 210/603, 614, 143; 137/2, 12, 14
See application file for complete search history.

(56) References Cited

U.S. PATENT DOCUMENTS

| | | |
|---|---|---|
| 2001/0005812 A1 | 6/2001 | Brookshire |
| 2011/0231099 A1 | 9/2011 | Elkins |
| 2011/0303299 A1* | 12/2011 | Martens .............. C12M 21/04 137/12 |

* cited by examiner

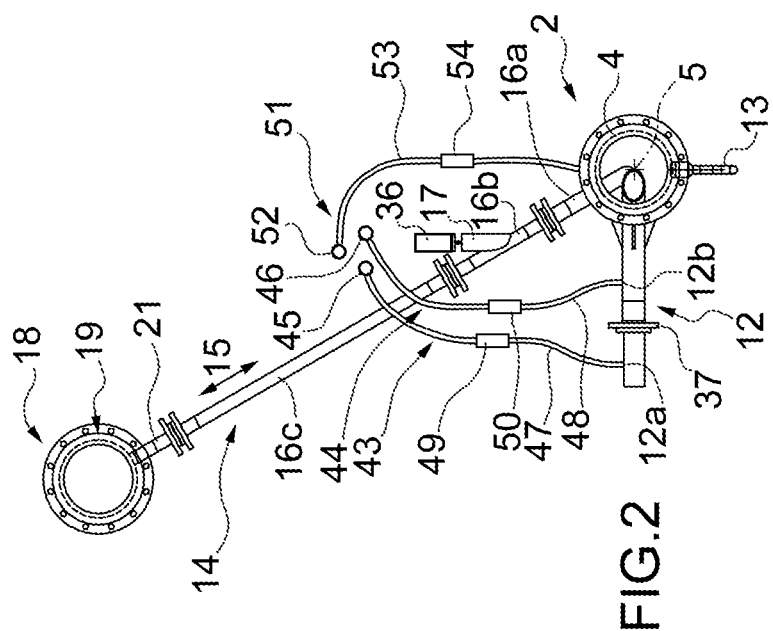
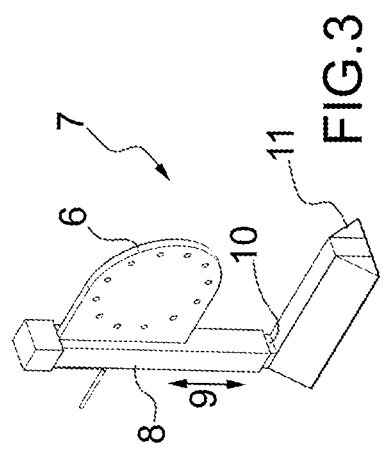
FIG.2
FIG.3
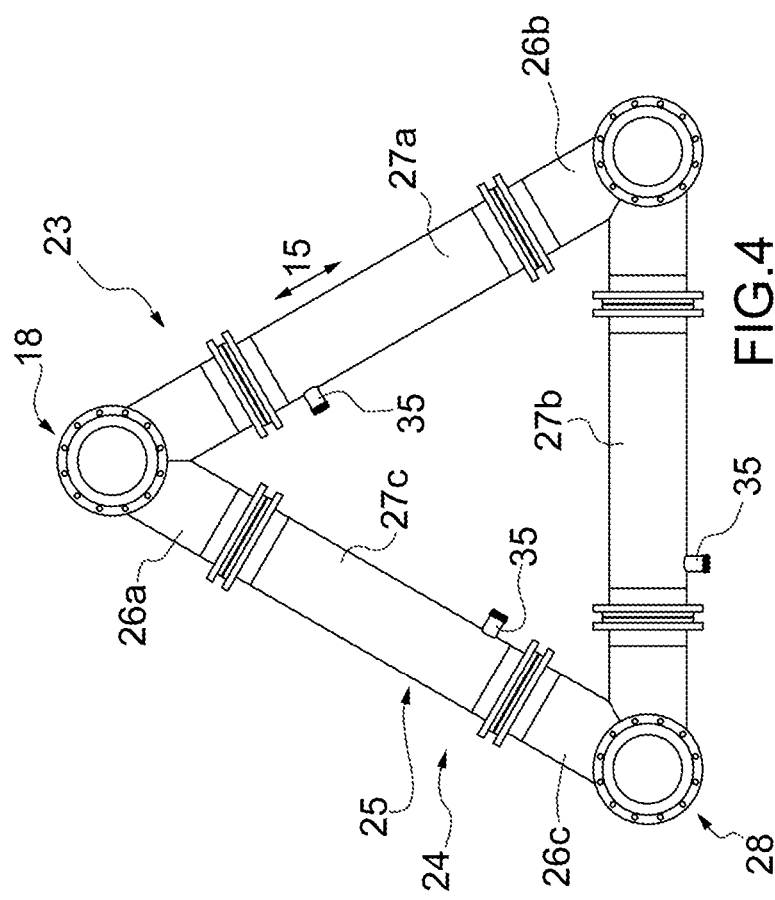
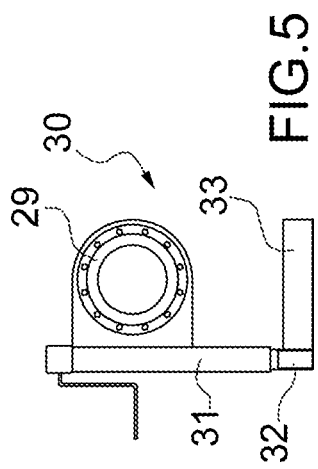
FIG.4
FIG.5

SYSTEM AND METHOD TO CONTROL A BIOGAS COLLECTION PLANT

CROSS-REFERENCE TO RELATED APPLICATION

The present application is a national phase entry under 35 U.S.C. § 371 of International Application No. PCT/IB2016/056844, filed Nov. 14, 2016, which designates the United States of America, and claims priority to Italian Application No. 102015000072559, filed Nov. 13, 2015, the entire disclosures of each are hereby incorporated by reference for all purposes.

TECHNICAL FIELD

The present invention concerns a system to control a biogas collection plant and a corresponding control method.

BACKGROUND ART

In the technical field of waste disposal, it is known that the biogas generated by the natural fermentation of solid organic waste masses contained in storage wells, also known as biogas capturing wells, is extracted, and the biogas extracted from the wells is collected by means of a biogas collection plant. The biogas capturing wells together with the biogas collection plant form a so-called biogas capturing system.

A landfill in general comprises a large number of wells, in the order of fifteen per hectare of landfill surface. The biogas collection plant is composed of several biogas collection stations, each of which is connected to the large number of wells, in general 10 to 20, by means of pipes to collect the biogas produced by said wells. In the biogas collection stations, a first discharge of the condensate generated by the biogas is performed.

The wells are different from one another and the minimum parameters that must be considered to optimize capturing of the biogas are the flow rate, the concentration of methane and oxygen in the biogas mixture and the depression applied to the well for the capturing.

Regulation of the biogas capturing by the wells is performed manually for each well, at best once every two days, according to manual analyses of flow rate, depression and concentration of methane and oxygen in the biogas using portable instruments which can be connected at predefined points of the biogas collection stations. Complete manual regulation of each well requires approximately 10 minutes.

A medium-sized landfill in general has a capturing system consisting of approximately 120 wells connected to approximately 10 biogas collection stations. The analysis and manual regulation of an entire capturing system obviously results in low efficiency and precision. In particular, the regulation technique described above has the following problems:

- the interpretation of the regulation is subjective, and therefore the efficiency of the capturing system depends on the ability of the operator in charge;
- the capturing system is not able to track the inevitable physical changes in the biogas throughout the day and any variations in suction conditions in the capturing lines during the day due to imperfect operation of the machines that generate the depression in the pipes of said lines; and
- impossibility of knowing the status of the capturing lines in terms of presence or absence of condensate, which limits capturing of the biogas.

DISCLOSURE OF INVENTION

The object of the present invention is to provide a method to control the biogas collection plant, which is free from the drawbacks described above and, at the same time, is easy and inexpensive to produce.

According to the present invention, a system and method to control a biogas collection plant are provided, as defined in the attached claims.

BRIEF DESCRIPTION OF THE DRAWINGS

The present invention will now be described with reference to the accompanying drawings, which illustrate a non-limiting embodiment example thereof, in which:

FIG. 2 is a lateral view of a first detail of FIG. 1;

FIG. 3 is a perspective view of a second detail of FIG. 1;

FIG. 4 is a lateral view of a third detail of FIG. 1; and

FIG. 5 is a lateral view of a fourth detail of FIG. 1.

BEST MODE FOR CARRYING OUT THE INVENTION

Figure 1:
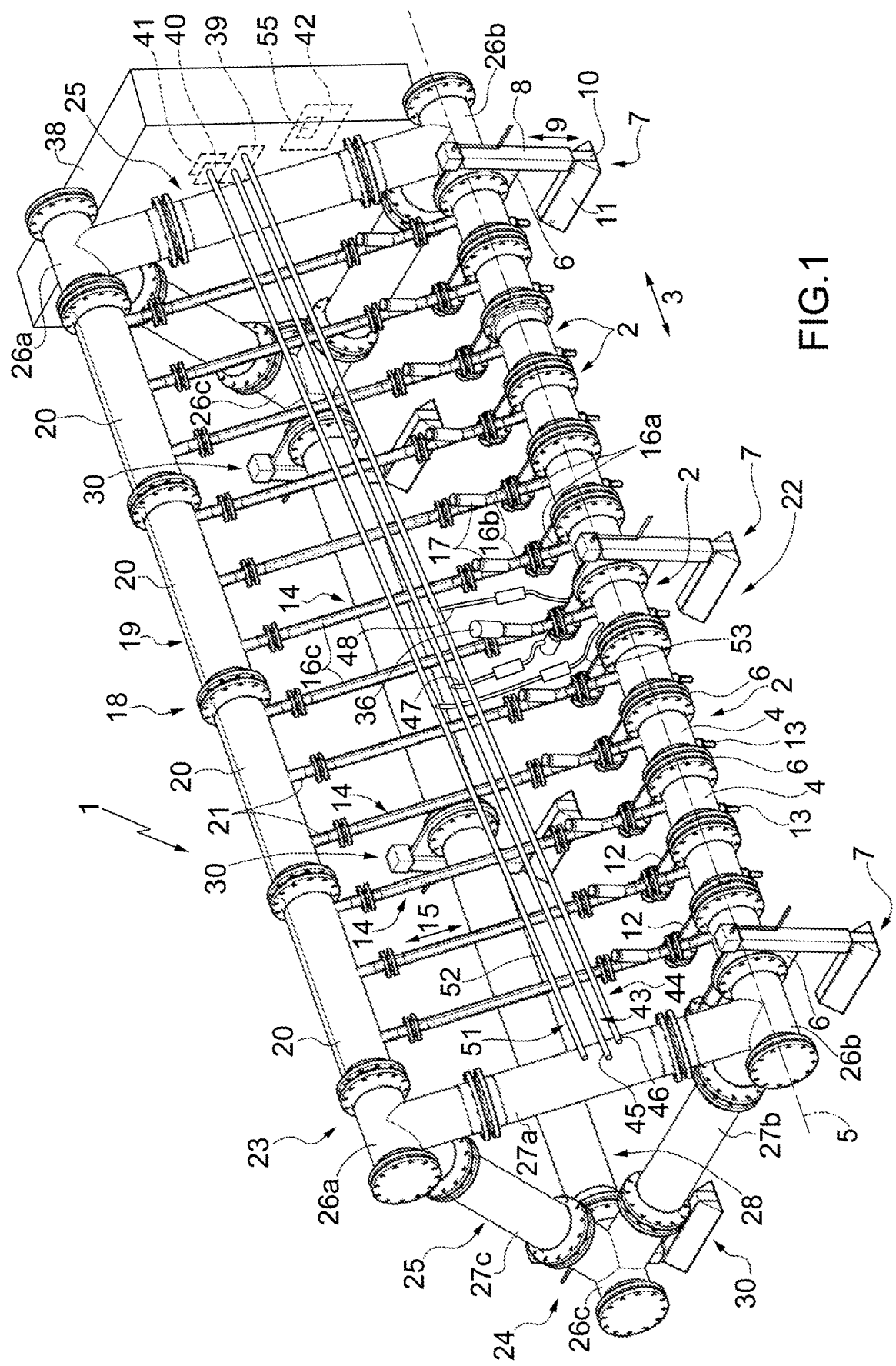
FIG. 1 is a schematic perspective view of a biogas collection plant to which the control method of the present invention is applied.

In FIG. 1, the number 1 generically indicates, overall, a biogas collection plant consisting of a single biogas collection station to collect the biogas generated by the natural fermentation of organic solid waste masses stored in capturing wells, known per se and therefore not illustrated. The plant 1, i.e. the collection station, comprises a plurality of collection units 2, in this case twelve collection units 2, which are connected to respective capturing wells, are mounted parallel to one another and are aligned with one another in a given direction 3.

With reference to FIGS. 1, 2 and 3, each collection unit 2 comprises a substantially cylindrical inlet sleeve 4, which has a longitudinal axis 5 parallel to the direction 3, is aligned with the inlet sleeves 4 of the other collection units in the direction 3, is mechanically connected to two adjacent inlet sleeves 4, and is separated in a fluid-dynamic manner from each adjacent inlet sleeve 4 by means of a substantially circular plate 6 mounted orthogonally to the axis 5. A plate 6 is provided to close each of the two outer inlet sleeves 4 (FIG. 1).

The plate 6 interposed between the two central inlet sleeves 4 and the two plates 6 closing the outer inlet sleeves 4 each define part of a respective supporting device 7 for the plant 1. Each supporting device 7 further comprises a box guide 8, which is fixed to the respective plate 6, extends in a direction 9 transverse to the direction 3, and is engaged slidingly by a slide 10 provided with a supporting foot 11 mounted at a lower free end of the slide 10 projecting on the outside of the guide 8. The position of the slides 10, and therefore of the feet 11 along the relative guides 8 in the direction 9, is adjusted to maintain the direction 3 in a horizontal position and the direction 9 in a vertical position so as to guarantee correct positioning of the plant 1 on the ground.

Each inlet sleeve 4 is provided with an inlet pipe 12 and an outlet pipe 13. The inlet pipe 12 extends transversally to the axis 5, projecting radially towards the outside from the inlet sleeve 4, and can be connected to the relative capturing well to feed the biogas generated in the capturing well into the inlet sleeve 4. The outlet pipe 13 extends in the direction 9 and projects radially downwards from the outer surface of the inlet sleeve 4 to discharge the condensate generated by the biogas inside the inlet sleeve 4 to the outside of the collection unit 2.

Each collection unit 2 comprises a feeding pipe 14, which projects radially towards the outside from the relative inlet sleeve 4, extends in a direction 15 inclined by an angle different from 0°, preferably approximately 30°, with respect to the direction 9, is parallel to the feeding pipes 14 of the other collection units 2, and comprises, in this case, three portions 16a, 16b, 16c connected to one another in a fluid-dynamic manner. The portion 16a is an inlet portion connected in a fluid-dynamic manner to the relative inlet sleeve 4, the portion 16b is an intermediate portion provided with a flow rate control valve 17 of known type, and the portion 16c is an outlet portion.

With particular reference to FIG. 1, the plant 1 comprises a manifold 18 for collection of the biogas fed through the inlet sleeves 4 and along the feeding pipes 14. The manifold 18 comprises a main pipe 19, which extends in the direction 3, and comprises, in turn, four portions 20 connected to one another in a fluid-dynamic manner. The manifold 18 comprises, for each feeding pipe 14, a secondary pipe 21, which extends in the direction 15, to connect in a fluid-dynamic manner the main pipe 19 to the feeding pipe 14.

The inlet sleeves 4, the support devices 7, and the manifold 18 define a first portion 22 of a support structure 23 of the plant 1 further comprising a second portion 24 adapted to stabilize the first portion 22 and comprising, in turn, two tubular support frames 25, which are arranged on opposite sides of the assembly formed by the inlet sleeves 4 and manifold 18 in the direction 3 and have a substantially triangular form.

With reference to FIGS. 1 and 4, each frame 25 comprises three four-way couplings 26a, 26b and 26c connected in a fluid-dynamic manner to one another in pairs by means of relative intermediate pipes 27a, 27b and 27c. The pipe 27a is parallel to the direction 15, the pipe 27b is substantially orthogonal to the directions 3 and 9 and the pipe 27c is arranged according to an angle substantially equal to 60° with respect to the pipes 27a and 27b. In each frame 25, the coupling 26a is connected in a fluid-dynamic manner to a relative free end of the manifold 18, the coupling 26b is connected to a relative outer inlet sleeve 4 by interposition of the plate 6 of the relative support device 7, and the coupling 26c is connected in a fluid-dynamic manner to a relative free end of a pipe 28 of the second portion 24 which extends parallel to the direction 3.

With reference to FIGS. 1 and 5, each coupling 26c is connected to the pipe 28 by interposition of an annular disc defining part of a relative support device 30, which further comprises a box guide 31, which is fixed to the disc 29, extends in the direction 9, and is engaged slidingly by a slide 32 provided with a supporting foot 33 mounted at a lower free end of the slide 32 projecting on the outside of the guide 31. Furthermore, the pipe 28 comprises two portions 34 connected to each other by interposition of the disc 29 of another support device 30. The position of the slides 32 and, therefore, of the feet 33 along the relative guides 31 in the direction 9 is adjusted analogously to what is described for the support devices 7 and for the same purpose.

With particular reference to FIG. 4, each frame 25 is provided with three outlet pipes 35 arranged at different heights in the direction 9 to discharge to the outside of the plant 1 at least part of the condensate generated by the biogas inside the manifold 18, the frames 25 and the pipe 28.

In use, the biogas generated inside the above-mentioned capturing wells enters the inlet sleeves 4 and passes through, in the following order, the feeding pipes 14, the manifold 18, the frames 25 and the pipe 28, and lastly is discharged to the outside of the plant 1 by means of at least one outlet (not illustrated) obtained in the manifold 18 and/or in the pipe 28 and/or in one of the frames 25.

The fluid-dynamic connection between the manifold 18 and the frames 25 and between the frames 25 and the pipe 28 allows the inlet sleeves 4 and the manifold 18 to define part of the support structure 23 and the biogas and/or the condensate generated by the biogas to flow into the frames 25 and pipe 28 and to give the support structure 23 a weight sufficient to stabilize the entire plant 1, avoiding the use of an auxiliary independent support structure on which to mount the collection units 2 and the manifold 18.

The support structure 23 is, therefore, a modular self-supporting structure, which incorporates inside it the inlet sleeves 4 and the manifold 18, has a relatively high versatility and flexibility, is symmetrical with respect to a substantially vertical plane of symmetry passing through the manifold 18, and can be mounted directly in the place of installation of the plant 1, considerably reducing the relative storage and transport costs.

According to the present invention, with reference to FIGS. 1 and 2, the plant 1 comprises a control system to automatically regulate capturing of the biogas via the plant 1. The control system comprises, for each collection unit 2, an electric actuator 36, which is coupled to the relative valve 17 to control the opening thereof, and a calibrated flange 37, which is arranged in the relative inlet pipe 12. FIG. 1 illustrates only an actuator 36 for the sake of simplicity. Each actuator 36 consists, for example, of 24 volt stepper motors. Indicating the percentage opening of the valve 17 by APE, the actuator 36 controls the opening APE from 0% to 100% in steps, for example, of 2.5%.

Furthermore, the control system comprises, shared between all the collection units 2: a control board 38, which houses a pressure sensor 39, a methane sensor 40, an oxygen sensor 41 and an electronic control unit 42 adapted to control the actuators 36 to regulate the opening of the respective valves 17 according to the processing of measurements taken by the sensors 39-41; two pressure monitoring networks 43 and 44, which connect in a fluid-dynamic manner the pressure sensor 39 to two points 12a and 12b of each inlet pipe 12 located upstream and downstream respectively of the relative calibrated flange 37 to allow measurement of the differential pressure P between the points 12a and 12b and the flow rate Q of biogas in the inlet pipe 12; and a chemical monitoring network 51, which connects in a fluid-dynamic manner the methane and oxygen sensors 40 and 41 to each inlet sleeve 4 to allow measurement of the percentage concentration of methane, indicated below by CH4, and the percentage concentration of oxygen, indicated below by O2, in the biogas mixture present in the inlet sleeve 4.

Each pressure monitoring network 43, 44 comprises a respective common pipe 45, 46 and, for each collection unit 2, a peripheral pipe 47, 48 connecting the respective point 12a, 12b of the relative inlet pipe 12 to the common pipe 45, 46. Each peripheral pipe 47, 48 is provided with a respective solenoid valve 49, 50 (FIG. 2) controlled by the control unit 42 to allow or block circulation of the biogas of the peripheral pipe 47, 48.

The chemical monitoring network 51 comprises a respective common pipe 52 and, for each collection unit 2, a peripheral pipe 53 connecting the relative inlet sleeve 4 to the common pipe 52. Each peripheral pipe 53 is provided with a respective solenoid valve 54 (FIG. 2) controlled by the control unit 42 to allow or block circulation of the biogas of the peripheral pipe 53.

The control system obviously comprises an electrical network (not illustrated) to wire the actuators 36 and the solenoid valves 49, 50 and 54 to the control board 38.

The solenoid valves 49, 50 and 54 are normally closed. The control unit 42 is configured to selectively control opening of the solenoid valves 49, 50 and 54 so as to measure the variable parameters indicated above by P, Q, CH4 and O2 for each collection unit 2. In particular, indicating by Pa and Pb the pressures measured at points 15a and 12b respectively of each collection unit 2, the control unit 42 calculates the differential pressure P relative to said collection unit 2 as the difference between the pressures Pb and Pa, or as a formula:

$$P=Pb-Pa.$$

The control unit 42 calculates the flow rate Q of each collection unit 2 as a function of the differential pressure P relative to the same collection unit 2 and the internal diameter of the calibrated flange 37.

The control unit 42 is configured to measure the parameters P, Q, CH4 and O2 for each collection unit 2 following two simultaneous time patterns. The measurements of the parameters P and Q are indirect, in the sense that, as explained previously, they are obtained by calculating them from the direct measurements of the pressures Pb and Pa. In both said time patterns, values measured of the parameters P, Q, CH4 and O2 are stored in a local memory of the control board 38, for example a memory 55 integrated in the control unit 42.

A first time pattern consists in assigning, to the collection units 2, respective time intervals (timeslots) $\Delta$Ti of equal duration and adjacent to one other so as to form a certain period of time TP1, the duration of which is equal to the sum of the time intervals $\Delta$Ti and, within each time interval $\Delta$Ti, controlling the opening of the solenoid valves 49, 50 and 54 of the relative collection unit 2 to measure the parameters P, Q, CH4 and O2 relative to said collection unit 2, processing the values measured and controlling the actuator 36 as a function of said processing to regulate the parameter APE, i.e. the percentage opening of the respective valve 17. The measurements of the parameters P, Q, CH4 and O2 are repeated cyclically on all the collection units 2 according to the period TP1. In other words, the period TP1 divided into the time intervals $\Delta$Ti defines a first cycle of measurements performed for all the collection units 2 in sequence which is repeated with period TP1.

Normally, the time interval $\Delta$Ti has a value selected from the range of values between 2 and 10 minutes to allow the measurements on a relative collection unit 2 and, at the same time, wait for a certain stabilization of the relative capturing well.

Within each time interval $\Delta$Ti, the control unit 42 is configured to measure the parameters P, Q, CH4 and O2 and process the values measured of the relative collection unit 2 according to two analysis methods described below.

According to a first analysis method, the control unit 42 controls the solenoid valves 49, 50 and 54 so as to measure, in the following order, the differential pressure P, the flow rate Q and lastly the concentrations of methane CH4 and oxygen O2. Before going on to measure the following parameter, the value measured of a parameter P, Q, CH4, O2 is compared with a relative predefined interval of values $\Delta$P, $\Delta$Q, $\Delta$CH4, $\Delta$O2, which is normally the same for all the collection units 2. The intervals $\Delta$P, $\Delta$Q, $\Delta$CH4 and $\Delta$O2 comprise values of the relative parameters P, Q, CH4 and O2 which correspond to a normal behaviour of a capturing well. Purely by way of example, the interval $\Delta$CH4 is between 1% and 50% and the interval $\Delta$O2 is between 1% and 10%.

If the value measured of the parameter P, Q, CH4, O2 is within the relative interval $\Delta$P, $\Delta$Q, $\Delta$CH4, $\Delta$O2, then the control unit 42 proceeds with measurement of the following parameter, otherwise it signals and records said event as a fault associated with the collection unit 2 in question and does not proceed with measurement of the other parameters that follow in the predefined order. The fault is recorded in the memory 55. The cause of said fault can be, for example, a mechanical problem with the valve 17, or obstruction of an inlet pipe 12.

The recording of a fault for a certain collection unit 2 entails the execution of a specific fault resolution action on the relative valve 17 which aims to resolve the fault, i.e. ensure that the parameters P, Q, CH4 and O2 return permanently within the relative intervals $\Delta$P, $\Delta$Q, $\Delta$CH4 and $\Delta$O2. The type of fault resolution action depends on which parameter P, Q, CH4, O2 lies outside the relative interval $\Delta$P, $\Delta$Q, $\Delta$CH4 and $\Delta$O2 and on the entity of the variance of the parameter from the relative interval. In other words, in the presence of a fault consisting of a parameter P, Q, CH4, O2 lying outside the relative interval $\Delta$P, $\Delta$Q, $\Delta$CH4, $\Delta$O2 for a certain collection unit 2, the control unit 42 controls the relative actuator 36 to perform, on the relative valve 17, an action selected from a group of actions comprising for example:

prolonged total closing (APE=0%);
temporary total closing; and
temporary total opening (APE=100%).

The prolonged total closing of the valve 17 can be re-set manually or automatically after a certain time interval greater than the time period TP1. The temporary total closing and the temporary total opening of the valve 17 have durations which can be selected from an interval, for example between 15 and 60 s. The control unit 14 selects the action to be performed on the valve 17 and the time duration of said action according to which parameter lies outside the relative interval and how far it lies outside said interval.

If the values measured of all the parameters P, Q, CH4 and O2 lie within the relative intervals $\Delta$P, $\Delta$Q, $\Delta$CH4 and $\Delta$O2, then the control unit 42 proceeds with the second analysis method.

It should be noted that measurement of the parameters CH4 and O2 requires much more time than measurement of the parameters P and Q. In fact, for one single collection unit 2, measurement of the parameters CH4 and O2 requires approximately at least 2 minutes whereas measurement of the parameters P and Q requires approximately 20 seconds. Consequently, at the end of measurement of the parameters CH4 and O2, the parameters P and Q could have undergone a significant variation.

According to the second analysis method, the control unit 42 determines a variable value of the parameter APE according to the combination of values measured of the parameters CH4 and so as to maximize the parameter CH4, and consequently controls the actuator 36 to regulate opening of the relative valve 17. The values measured of the parameters CH4 and O2 used for determination of the parameter APE are those obtained with the first analysis method.

With the second analysis method, furthermore, after adjustment of the valve 17 with the above-mentioned value of the parameter APE, the control unit 42 controls the solenoid valves 49 and 50 to measure the parameters P and Q again and compare the relative new values measured with the previous values measured, stored in the memory 55, to verify whether there is a variance greater than the relative tolerances τP and τQ between the new and the previous values. If one or both of the variances of the parameters P and Q are outside the relative tolerances τP and τQ, then the control unit 42 records said event as a fault associated with the collection unit 2 in question and carries out a specific fault resolution action on the relative valve 17, of the same type as those described in relation to the first analysis method; otherwise the control unit 42 does nothing until the end of the relative time interval ΔTi.

The ultimate purpose of the adjustment of the valves 17 following the second analysis method is not so much to maximize for its own sake the parameter CH4 for each collection unit 2, but to maximize the calorific value of the biogas circulating in the collection unit 2, i.e. to maximize the parameter CH4 and at the same time guarantee the time stability of the parameters P and Q. In other words, the object of the second analysis method is to maximize the calorific value of the biogas sucked in by each collection unit 2 compatibly with the capacity of the relative capturing well to supply biogas.

In the second time pattern, the control unit 42 periodically controls opening of the solenoid valves 49 and 50 of all the collection units 2, in sequence one after the other, excluding the one which is analysed in the same time period following the first time pattern, according to a time period TP2 shorter than TP1, to measure the parameters P and Q relative to all the collection units 2. The time period TP2 is greater than or equal to the time required for measurement of the parameters P and Q, which is between approximately 15 and 30 seconds, multiplied by the number of collection units 2 of the plant 1. The second time pattern is simultaneous with the first time pattern and has the purpose of acquiring values measured of the parameters P and Q of all the collection units 2 at a higher rate than the one defined by the first measurement cycle. In other words, the second time pattern defines a second measurement cycle relative to the parameters P and Q of all the collection units 2. Since the common pipes 46 and 47 have to be shared with the first measurement cycle, the second measurement cycle must necessarily be synchronized with the first measurement cycle to be able to "skip" the collection unit 2 associated with the interval ΔTi during which said first measurement cycle is being performed.

The control unit 42 stores the values measured of the parameters P and Q in the memory 55 and compares the new values measured with the previous values measured relative to the previous cycle to verify whether there is a variance greater than the relative tolerances τP and τQ between the new values and the previous values. If one or both the variances of the parameters P and Q exceed the relative tolerances τP and τQ, then the control unit 42 records said event as a fault associated with the collection unit 2 in question and performs a specific fault resolution action on the relative valve 17, of the same type as those described in relation to the first analysis method.

According to a further embodiment not illustrated of the present invention, derived from the one illustrated by FIGS. 1 to 5, the control system of the plant 1 is without the calibrated flanges 37 and the pressure monitoring network and comprises a total pressure monitoring pipe, which connects in a fluid-dynamic manner the pressure sensor 39 to the four-way coupling 26*a* (the higher one) of one of the frames 25 or to one of the portions 20 of the main pipe 19 of the manifold 18 and is provided with a respective solenoid valve controlled by the control unit 42 to allow measurement of the total pressure Ptot inside the manifold 18. Consequently, each collection unit 2 has one single pressure measurement point, i.e. point 12*a*. The control unit 42 is configured to calculate the differential pressure P as the difference between the pressure Ptot and the pressure Pa, i.e.:

$$P = Ptot - Pa,$$

and the flow rate Q as a function of the pressure Pa and of a measurement of the opening APE. The control unit 42 is able to measure indirectly the opening APE of each valve 17 from knowledge of the angular position of the relative actuator 36.

According to variations of the above-mentioned further embodiment, each peripheral pipe 47 of the sole pressure monitoring network 43 is connected at any point of the fluid-dynamic path defined by the relative collection unit 2 upstream of the valve 17, with respect to the direction of circulation of the biogas inside the relative feeding pipe 14, for example at a point of the feeding pipe 14 located between the valve 17 and the inlet sleeve 4.

According to a further embodiment not illustrated of the present invention, derived from the one illustrated by FIGS. 1 to 5, the chemical monitoring network 54 comprises a further peripheral pipe, which connects in a fluid-dynamic manner the common pipe 52 to the four-way coupling 26*a* (the higher one) of one of the frames 25 or to one of the portions 20 of the main pipe 19 of the manifold 18 and is provided with a respective solenoid valve controlled by the control unit 42 to allow measurement of the total concentration of methane CH4tot and the total concentration of oxygen O2tot inside the manifold 18. The control unit 42 is configured to vary the intervals ΔCH4 and ΔO2 as a function of the values measured of total concentration of methane CH4tot and total concentration of oxygen O2tot in order to optimize the performance of the plant 1 in relation to the overall characteristics of the capturing wells connected to said plant 1.

According to a further embodiment not illustrated of the present invention, derived from the one illustrated by FIGS. 1 to 5, the control system of the plant 1 comprises the above-mentioned total pressure monitoring pipe to measure the total pressure Ptot inside the manifold 18, the chemical monitoring network 54 comprises the above-mentioned further peripheral pipe to measure the total concentration of methane CH4tot and the total concentration of oxygen O2tot inside the manifold 18, and the control unit 42 is configured to vary the intervals ΔP, ΔCH4 and ΔO2 as a function of the total pressure values measured Ptot, total concentration of methane CH4tot and total concentration of oxygen O2tot in order to optimize the performance of the plant 1 in relation to the overall characteristics of the capturing wells connected to said plant 1.

According to variations not illustrated:
- each feeding pipe 14 and/or the manifold 18 and/or each frame 25 and/or the pipe 28 are made in one single piece;
- the frames 25 are separated from the manifold 18 and the second portion 24 of the support structure 23 is filled and stabilized by means of a further fluid fed into the second portion 24;
- the inlet sleeves 4 are connected to one another in a fluid-dynamic manner;
- the outer inlet sleeves 4 are connected to the frames 25 in a fluid-dynamic manner; and the pressure and chemical monitoring networks comprise pneumatic valves instead of the solenoid valves.

The invention claimed is:

1. A control system to control a biogas collection plant comprising a collection manifold and a plurality of collection units, each of which is connected to a respective capturing well and comprises a respective feeding pipe connected to the collection manifold and a respective regulation valve to adjust a biogas flow rate in the feeding pipe itself; the control system comprising a plurality of actuators, each of which is designed to adjust opening of a respective regulation valve, a control board, which comprises a pressure sensor, a methane sensor, an oxygen sensor and a control unit, at least one first biogas pressure monitoring network, which is designed to connect the pressure sensor to the collection units in a fluid-dynamic manner and comprises, for each collection unit, a respective first control valve, and a chemical biogas monitoring network, which is designed to connect the methane sensor and the oxygen sensor to the collection units in a fluid-dynamic manner and comprises, for each collection unit, a respective second control valve; the control unit being configured to selectively control said first and second control valves so as to measure, for each collection unit, a first pressure, a methane concentration and an oxygen concentration of the biogas in the collection unit, and to control an actuator of said plurality of actuators which is associated with the collection unit, as a function of a processing of measured values of the first pressure and the methane and oxygen concentrations.

2. A control system according to claim 1, wherein said first biogas pressure monitoring network connects said pressure sensor in a first point of each collection unit of said plurality of collection units upstream of the regulation valve, relative to the direction of circulation of the biogas in the feeding pipe, so that the first pressures measured for the collection unit relates to the biogas in said first point.

3. A control system according to claim 1, wherein said control unit is configured to determine, for each collection unit, a differential pressure as a function of a reference pressure and of said first pressure, and a biogas flow rate in the collection unit as a function of said first pressure, and to control the relative actuator of the collection unit as a function of the differential pressure, the flow rate and the methane and oxygen concentrations.

4. A control system according to claim 3, wherein said first biogas pressure monitoring network connects said pressure sensor in a first point of each collection unit of said plurality of collection units upstream of the regulation valve, relative to the direction of circulation of the biogas in the feeding pipe, so that the first pressure measured for the collection unit relates to the biogas in said first point, and each collection unit comprises an inlet pipe that can be connected to the respective capturing well; the control system comprising a plurality of calibrated flanges, each calibrated flange of said plurality of calibrated flanges being mountable in the inlet pipe of a respective collection unit so said first point is upstream of the calibrated flange, and a second biogas pressure monitoring network, which is designed to connect, in a fluid-dynamic manner, the pressure sensor to the inlet pipe of each collection unit in a second point downstream of the calibrated flange and comprises, for each collection unit, a respective third control valve; said control unit being configured to selectively control the third control valves so as to measure, for each collection unit, said reference pressure as the pressure of the biogas in the second point and to determine said flow rate as a function of the differential pressure and of the inner diameter of the calibrated flange.

5. A control system according to claim 3 and comprising a total biogas pressure monitoring pipe, which is designed to connect the pressure sensor to the collection manifold in a fluid-dynamic manner and is provided with a fourth control valve controlled by said control unit so as to allow the reference pressure to be measured as the pressure of the biogas in the collection manifold; the control unit being configured to determine said flow rate of each collection unit as a function of the first pressure and of the percentage opening of the regulation valve.

6. A biogas collection plant comprising a collection manifold, a plurality of collection units, each of which is connectable to a respective capturing well and comprises a respective feeding pipe connected to the collection manifold and a respective regulation valve to adjust the biogas flow rate in the feeding pipe itself, and a control system according to claim 1.

7. A method to control a biogas collection plant comprising a collection manifold and a plurality of collection units, each of which is connected to a respective capturing well and comprises a respective feeding pipe connected to the collection manifold and a respective regulation valve to adjust a biogas flow rate in the feeding pipe itself; the method comprising:
   carrying out a first periodic cycle of measurements of parameters of the biogas in the collection units by means of a group of sensors shared by all collection units, the first periodic cycle of measurements being divided into a plurality of time intervals, in each time interval of said plurality of time intervals the parameters of a respective collection unit being measured;
   carrying out a second periodic cycle of measurements of a sub-set of the parameters of the biogas in the collection units by means of a sub-set of the group of sensors, the second cycle of measurements being simultaneous with and having a smaller periodicity than the first cycle of measurements;
   in each time interval, adjusting the opening of the regulation valve of the collection unit as a function of the processing of the measured values of the parameters obtained in the time interval; and
   detecting possible faults in each collection unit as a function of the processing of the measured values of the sub-set of parameters obtained in the second cycle of measurements.

8. A method according to claim 7, wherein said group of sensors comprises a pressure sensor, a methane sensor and an oxygen sensor and said sub-set of the group of sensors comprises said pressure sensor.

9. A method according to claim 8, wherein said parameters comprise a pressure, a biogas methane concentration and a biogas oxygen concentration.

10. A method according to claim 8, wherein said parameters comprise a differential pressure, which is determined as a function of a reference pressure and a first pressure measured in a first point of the collection unit, and a flow rate of the biogas in the collection unit, which is determined as a function of the first pressure.

11. A method according to claim 10, wherein each collection unit comprises an inlet pipe, which can be connected to the respective capturing well and is provided with a respective calibrated flange; said first point being arranged upstream of the calibrated flange; said reference pressure being a pressure measured for each collection unit in a second point of the inlet pipe downstream of the calibrated flange; said flow rate of the biogas in the collection unit being determined as a function of said differential pressure and of an inner diameter of the calibrated flange.

12. A method according to claim 10, comprising:
   measuring said reference pressure in said collection manifold by means of said pressure sensor;
   said flow rate of the biogas in the collection unit being determined as a function of said first pressure and of the opening of the regulation valve.

13. A method according to claim 10, wherein said first point of the collection unit is upstream of the regulation valve of the collection unit, relative to the direction of circulation of the biogas in the feeding pipe.

14. A method according to claim 8, wherein said biogas collection plant comprises: at least one first biogas pressure monitoring network, which is adapted to connect the pressure sensor to said collection units in a fluid-dynamic manner and comprises, for each collection unit, a respective first control valve; and a chemical biogas monitoring network, which is adapted to connect the methane sensor and the oxygen sensor to the collection units in a fluid-dynamic manner and comprises, for each collection unit, a respective second control valve; in each time intervals of said first periodic cycle of measurements, the first and the second control valve of the collection unit being controlled to allow measurement of said parameters and in said second periodic cycle of measurements the first control valves being controlled in sequence one after the other, excluding the first control valve of the collection unit which in the same time period is analysed by the first measurement cycle, to allow measurement of said subset of parameters.

15. A method according to claim 7, wherein said first cycle of measurements comprises, for each time interval:
   associating each one of said parameters with a respective predetermined interval of values indicating a normal behaviour of a capturing well; and
   measuring each parameter and comparing the measured value with the respective interval of values;
   in each time interval, the opening of the regulation valve of the collection unit being adjusted if the measured values of each parameters lie within the respective interval of values.

16. A method according to claim 15, wherein said first cycle of measurements comprises, for each time interval:
   if the measured value of at least one of said parameters is outside of the respective interval of values, then a fault associated with the collection unit is recorded.

17. A method according to claim 15, wherein said parameters comprise differential pressure, which is determined as a function of a reference pressure and a first pressure measured in a first point of the collection unit, a flow rate of the biogas in the collection unit, which is determined as a function of the first pressure, a biogas methane concentration and a biogas oxygen concentration, and measuring each parameter and comparing the measured value with the respective interval of values comprises:
   measuring, in the following order, differential pressure, flow rate, methane concentration and oxygen concentration;
   for each measured parameter, comparing the measured value with the respective predetermined interval of values; and
   moving on to the measurement of the following parameter, according to said order, only if the measured value lies within the respective predetermined value interval.

18. A method according to claim 7, wherein said parameters comprise a biogas methane concentration and a biogas oxygen concentration; in each time interval, the opening of the regulation valve of the collection unit being adjusted as a function of the combination of the measured values of the biogas methane concentration and the biogas oxygen concentrations obtained in the time interval, in such a way as to maximise the biogas methane concentration.

* * * * *